US010611131B2

United States Patent
Langford et al.

(10) Patent No.: US 10,611,131 B2
(45) Date of Patent: Apr. 7, 2020

(54) PERFORATED STRETCH LAMINATE

(71) Applicant: Aplix, Le Cellier (FR)

(72) Inventors: Bradley Langford, Fort Mill, SC (US);
Donald H. Lester, Jr., Charlotte, NC (US)

(73) Assignee: Aplix, Le Cellier (FR)

( * ) Notice: Subject to any disclaimer, the term of this patent is extended or adjusted under 35 U.S.C. 154(b) by 176 days.

(21) Appl. No.: 15/489,812

(22) Filed: Apr. 18, 2017

(65) Prior Publication Data
US 2017/0297313 A1 Oct. 19, 2017

Related U.S. Application Data

(60) Provisional application No. 62/324,574, filed on Apr. 19, 2016.

(51) Int. Cl.
*B32B 3/24* (2006.01)
*B32B 5/02* (2006.01)
(Continued)

(52) U.S. Cl.
CPC ........ *B32B 27/12* (2013.01); *A61F 13/15577* (2013.01); *A61F 13/4902* (2013.01); *A61F 13/5622* (2013.01); *B32B 3/266* (2013.01); *B32B 5/022* (2013.01); *B32B 5/04* (2013.01); *B32B 7/04* (2013.01); *B32B 7/12* (2013.01);
(Continued)

(58) Field of Classification Search
None
See application file for complete search history.

(56) References Cited

U.S. PATENT DOCUMENTS

D99,619 S * 5/1936 Daniels .............................. D5/1
2,068,456 A * 1/1937 Hooper .................. A41D 31/02
428/138
(Continued)

FOREIGN PATENT DOCUMENTS

EP 1528133 A1 * 5/2005 ....... A61F 13/15707
EP 1598172 A1 * 11/2005 ............... B29D 7/01
(Continued)

OTHER PUBLICATIONS

IPS Perforating, Inc., "Perforating materials for product manufactures nationwide," http://ipsperforating.com/, 2015.

*Primary Examiner* — Jeffrey A Vonch
(74) *Attorney, Agent, or Firm* — Hammer & Associates, P.C.

(57) ABSTRACT

A stretch laminate and a method for reducing and/or preventing tearing in a stretch laminate, when the stretch laminate is stretched in a stretching direction, is disclosed. The stretch laminate has a perforation pattern. The perforation pattern has at least two columns. A first column has a plurality of pairs of perforations stacked one pair above the other pair. The perforations in each pair sloping in a first direction, and a first space separating one pair from the other pair. A second column has a plurality of pairs of perforations stacked one pair above the other pair. The perforations in each pair sloping in a second direction, and a second space separating one pair from the other pair. The first direction and the second direction may be different. A third space between the columns is no greater than the first or second space between perforation in the pair.

22 Claims, 6 Drawing Sheets

(51) Int. Cl.

| | | |
|---|---|---|
| *B32B 5/26* | (2006.01) | |
| *B32B 25/10* | (2006.01) | |
| *B32B 27/12* | (2006.01) | |
| *B32B 7/04* | (2019.01) | |
| *A61F 13/49* | (2006.01) | |
| *A61F 13/15* | (2006.01) | |
| *B32B 5/04* | (2006.01) | |
| *A61F 13/56* | (2006.01) | |
| *B32B 27/30* | (2006.01) | |
| *B32B 7/12* | (2006.01) | |
| *B32B 27/40* | (2006.01) | |
| *B32B 25/16* | (2006.01) | |
| *B32B 27/32* | (2006.01) | |
| *B32B 7/14* | (2006.01) | |
| *B32B 27/34* | (2006.01) | |
| *B32B 27/36* | (2006.01) | |
| *B32B 3/26* | (2006.01) | |

(52) U.S. Cl.
CPC .............. *B32B 7/14* (2013.01); *B32B 25/10* (2013.01); *B32B 25/16* (2013.01); *B32B 27/302* (2013.01); *B32B 27/32* (2013.01); *B32B 27/34* (2013.01); *B32B 27/36* (2013.01); *B32B 27/40* (2013.01); *B32B 2250/02* (2013.01); *B32B 2250/03* (2013.01); *B32B 2250/40* (2013.01); *B32B 2262/0253* (2013.01); *B32B 2262/0261* (2013.01); *B32B 2262/0284* (2013.01); *B32B 2262/14* (2013.01); *B32B 2307/51* (2013.01); *B32B 2307/5825* (2013.01); *B32B 2307/718* (2013.01); *B32B 2307/724* (2013.01); *B32B 2307/732* (2013.01); *B32B 2555/02* (2013.01); *Y10T 428/24273* (2015.01); *Y10T 428/24298* (2015.01); *Y10T 428/24322* (2015.01); *Y10T 442/659* (2015.04); *Y10T 442/674* (2015.04); *Y10T 442/678* (2015.04); *Y10T 442/679* (2015.04)

(56) References Cited

U.S. PATENT DOCUMENTS

| | | | | |
|---|---|---|---|---|
| 2,115,122 A * | 4/1938 | Prudden | B65D 85/808 | 426/81 |
| 3,085,024 A * | 4/1963 | Blackford | C09J 7/20 | 428/43 |
| 3,183,116 A * | 5/1965 | Schaar | A61F 13/0226 | 427/208.6 |
| 3,655,501 A * | 4/1972 | Tesch | A47G 27/00 | 428/136 |
| 4,075,382 A * | 2/1978 | Chapman | A47K 10/16 | 428/192 |
| 4,275,105 A * | 6/1981 | Boyd | D04H 1/60 | 428/198 |
| 4,414,970 A * | 11/1983 | Berry | A61F 13/00038 | 602/75 |
| 4,451,520 A * | 5/1984 | Tecl | D04H 1/54 | 428/195.1 |
| 5,336,554 A | 8/1994 | Knight | | |
| 5,536,555 A * | 7/1996 | Zelazoski | A61F 13/512 | 428/138 |
| 5,571,096 A * | 11/1996 | Dobrin | A61F 13/5146 | 604/383 |
| 5,964,742 A * | 10/1999 | McCormack | D04H 1/54 | 604/380 |
| 6,039,906 A * | 3/2000 | Sageser | B26F 1/24 | 264/156 |
| 6,069,097 A * | 5/2000 | Suzuki | A61F 13/49009 | 442/328 |
| 6,106,925 A * | 8/2000 | Palumbo | A61F 13/512 | 428/137 |
| 6,537,930 B1 * | 3/2003 | Middlesworth | A61F 13/5146 | 428/137 |
| D475,206 S * | 6/2003 | Ackerman | D5/57 | |
| 6,610,390 B1 * | 8/2003 | Kauschke | B32B 5/26 | 428/198 |
| 6,620,490 B1 * | 9/2003 | Malchow | B32B 7/04 | 428/196 |
| 6,635,334 B1 * | 10/2003 | Jackson | B32B 3/10 | 428/136 |
| 6,713,159 B1 * | 3/2004 | Blenke | A61F 13/496 | 428/195.1 |
| 6,717,028 B1 * | 4/2004 | Oberstadt | A61F 13/515 | 604/365 |
| 7,794,819 B2 | 9/2010 | Black et al. | | |
| D637,008 S * | 5/2011 | Frost | D5/4 | |
| 8,795,809 B2 | 8/2014 | Mansfield | | |
| D747,887 S * | 1/2016 | Seitzinger | D5/57 | |
| 2001/0008676 A1 * | 7/2001 | Pelkie | B29D 7/01 | 428/136 |
| 2002/0016122 A1 * | 2/2002 | Curro | A47L 1/15 | 442/381 |
| 2002/0048652 A1 * | 4/2002 | Malchow | A61F 13/15756 | 428/194 |
| 2002/0156444 A1 * | 10/2002 | Otsubo | A61F 13/51464 | 604/385.3 |
| 2002/0182371 A1 * | 12/2002 | Soon | A61F 13/4902 | 428/137 |
| 2003/0022582 A1 * | 1/2003 | Cree | A61F 13/4902 | 442/394 |
| 2003/0084986 A1 * | 5/2003 | Cree | A61F 13/5146 | 156/229 |
| 2003/0105446 A1 * | 6/2003 | Hutson | A61F 13/4902 | 604/385.22 |
| 2004/0122404 A1 * | 6/2004 | Meyer | A61F 13/49012 | 604/385.19 |
| 2004/0241389 A1 * | 12/2004 | Chung | A61F 13/4902 | 428/131 |
| 2005/0123721 A1 * | 6/2005 | Heikaus | B29C 66/4722 | 428/137 |
| 2006/0149209 A1 * | 7/2006 | Malchow | A61F 13/49 | 604/389 |
| 2006/0247591 A1 * | 11/2006 | Hughes | A61F 13/49012 | 604/383 |
| 2007/0123124 A1 * | 5/2007 | Middlesworth | A61F 13/4902 | 442/59 |
| 2007/0144693 A1 * | 6/2007 | Ruthven | A61F 13/15731 | 162/117 |
| 2007/0233034 A1 * | 10/2007 | Hildeberg | A61F 13/15203 | 604/385.24 |
| 2007/0249253 A1 * | 10/2007 | Angeli | B32B 27/12 | 442/394 |
| 2008/0051748 A1 * | 2/2008 | Black | B32B 37/144 | 604/385.01 |
| 2008/0140038 A1 * | 6/2008 | Sasayama | A61F 13/15739 | 604/367 |
| 2009/0208703 A1 * | 8/2009 | Wennerback | A61F 13/15707 | 428/138 |
| 2009/0292266 A1 * | 11/2009 | Back | A61F 13/15739 | 604/365 |
| 2010/0059067 A1 * | 3/2010 | Frank | A61F 13/515 | 128/849 |
| 2010/0215923 A1 * | 8/2010 | Frost | B32B 27/32 | 428/196 |
| 2010/0262105 A1 * | 10/2010 | Turner | A61F 13/4902 | 604/366 |
| 2010/0268183 A1 * | 10/2010 | Een | A61F 13/15739 | 604/385.01 |
| 2011/0250413 A1 * | 10/2011 | Lu | D04H 1/62 | 428/196 |
| 2012/0128927 A1 * | 5/2012 | Tasi | B32B 38/0032 | 428/131 |
| 2012/0207969 A1 * | 8/2012 | Mansfield | A61L 15/24 | 428/131 |

(56) References Cited

U.S. PATENT DOCUMENTS

| | | | |
|---|---|---|---|
| 2012/0209230 A1* | 8/2012 | Mansfield | A61F 13/4902 604/361 |
| 2012/0244412 A1* | 9/2012 | Pascaly | B01D 67/0032 429/144 |
| 2012/0278975 A1* | 11/2012 | Yamashita | A61F 13/4963 2/400 |
| 2013/0164480 A1* | 6/2013 | Sakurai | B32B 5/14 428/56 |
| 2013/0299114 A1* | 11/2013 | Straub | D21F 1/0063 162/348 |
| 2015/0088088 A1* | 3/2015 | Wade | A61F 13/49012 604/396 |
| 2015/0297422 A1* | 10/2015 | Nelson | A61F 13/4902 604/365 |
| 2018/0028371 A1* | 2/2018 | Takaishi | A61F 13/49019 |
| 2018/0042784 A1* | 2/2018 | Koshijima | B32B 7/05 |

FOREIGN PATENT DOCUMENTS

| | | | | |
|---|---|---|---|---|
| JP | 10029259 A | * | 2/1998 | |
| JP | 2003339772 A | * | 12/2003 | |
| JP | 2005001272 A | * | 1/2005 | |
| JP | 2011147495 A | * | 8/2011 | |
| JP | 2012192058 A | * | 10/2012 | |
| JP | 2014233624 A | * | 12/2014 | B29C 65/08 |
| KR | 20120087530 A | * | 8/2012 | |
| WO | WO-9964238 A1 | * | 12/1999 | B32B 27/12 |

\* cited by examiner

PERFORATED STRETCH LAMINATE

RELATED APPLICATION

This application claims the benefit of U.S. Provisional Application Ser. No. 62/324,574 filed on Apr. 19, 2016.

FIELD OF THE INVENTION

The invention is directed to a perforated stretch laminate that may be used in the construction of hygiene products and a method of reducing or preventing tearing in a stretch laminate.

BACKGROUND OF THE INVENTION

Stretch laminates are used, for example, in the construction of hygiene products. Hygiene products may include, but are not limited to: diapers, absorbent articles, training pants, youth pants, adult incontinence products, and the like. For example, see U.S. Pat. No. 7,794,819 and the references cited therein, each of which is incorporated herein, in their entirety, by reference.

In general, stretch laminates may be structures having two or three layers laminated together, so that the laminated structure is elastic (e.g., stretchable and recoverable) in at least one direction. The two layer laminate typically includes a non-woven fabric (or film) laminated to an elastic film, and the three layer laminate typically includes two non-woven fabrics (or films) sandwiching the elastic film.

Stretch laminates may be used as various components of the hygiene product. In one example, the stretch laminate is used to form the 'side panel ears' or 'tabs' of the hygiene product. The side panel ears and tabs are used to secure the hygiene product around the waist of the wearer. Typically, the side panel ears or tabs are affixed to the lateral rear portions of the hygiene products, and may be releasably fastened to the front portion of the hygiene product, when that product is in use on the wearer.

These side panel ears or tabs are typically elastic. The elasticity of the side panel ears or tabs helps to insure a secure and snug fit of the hygiene product to the wearer. In use, for example, the side panel ears or tabs may be stretched from the rear portion of the product and around the wearer, and are releasably fastened to the front of the product, and the side panel ears or tabs retract to provide the secure and snug fit to the wearer.

These side panel ears and tabs may be breathable or non-breathable. Non-breathable side panel ears or tabs may be uncomfortable for wearers and may be prone to cause infections due to the high moisture content between the skin and non-breathable side panel ear. These products mimic traditional underwear design and could potentially be worn for longer periods of time as older children/adults have more control over their bladder. This longer wear time may also contribute to skin irritation/degradation due to moisture between the laminate and user. In particular, in countries where the atmosphere has a high temperature and/or high rate of humidity. Breathable side panel ears or tabs may be perforated. The perforations allow the moisture to escape and the skin to "breathe". But, the problem with perforating a film is the perforations make the ear inherently weak by providing a route for a tear propagation as the ear is stretched. The stretching could be made when the product is manufactured on a manufacturing line, and/or when activated, and/or when the product is rolled and/or unrolled in order to manufacture the hygiene article, and/or when the hygiene article is fit on the wearer or during use.

Accordingly, there is a need to make a breathable (e.g., perforated) stretch laminate that is resistant to tearing or tear propagation when stretched.

U.S. Pat. No. 5,336,554 discloses a stretchable tear resistant porous elastomeric film in which the perforation are made by laser beams. USD637008 shows a stretch laminate incorporating a design. US2012/0244412 discloses a perforated film. U.S. Pat. No. 8,795,809 discloses a tear resistant elastic film made with a SEEPS elastomeric block copolymer. IPS Hole Pattern 14.2 from International Perforating Services, Inc of Statesville, N.C. is a perforation pattern which is decorative and used for rigid supports, has good air flow and good acoustical properties (but makes no reference to resistance to tearing or tear propagation, in particular no reference about a stretch laminate). Each of the foregoing references are incorporated herein, in their entirety, by reference.

SUMMARY OF THE INVENTION

A stretch laminate and a method for reducing and/or preventing tearing in a stretch laminate, when the stretch laminate is stretched in a stretching direction, is disclosed. The stretch laminate has a perforation pattern. The perforation pattern has at least two columns. A first column has a plurality of pairs of perforations stacked one pair above the other pair. The perforations in each pair sloping in a first direction, and a first space separating one pair from the other pair. A second column has a plurality of pairs of perforations stacked one pair above the other pair. The perforations in each pair sloping in a second direction, and a second space separating one pair from the other pair. The first direction and the second direction may be different. A third space between the columns is no greater than the first or second space between perforation in the pair.

DESCRIPTION OF THE DRAWINGS

For the purpose of illustrating the invention, there is shown in the drawings a form that is presently preferred; it being understood, however, that this invention is not limited to the precise arrangements and instrumentalities shown.

DESCRIPTION OF THE INVENTION

Figure 1:
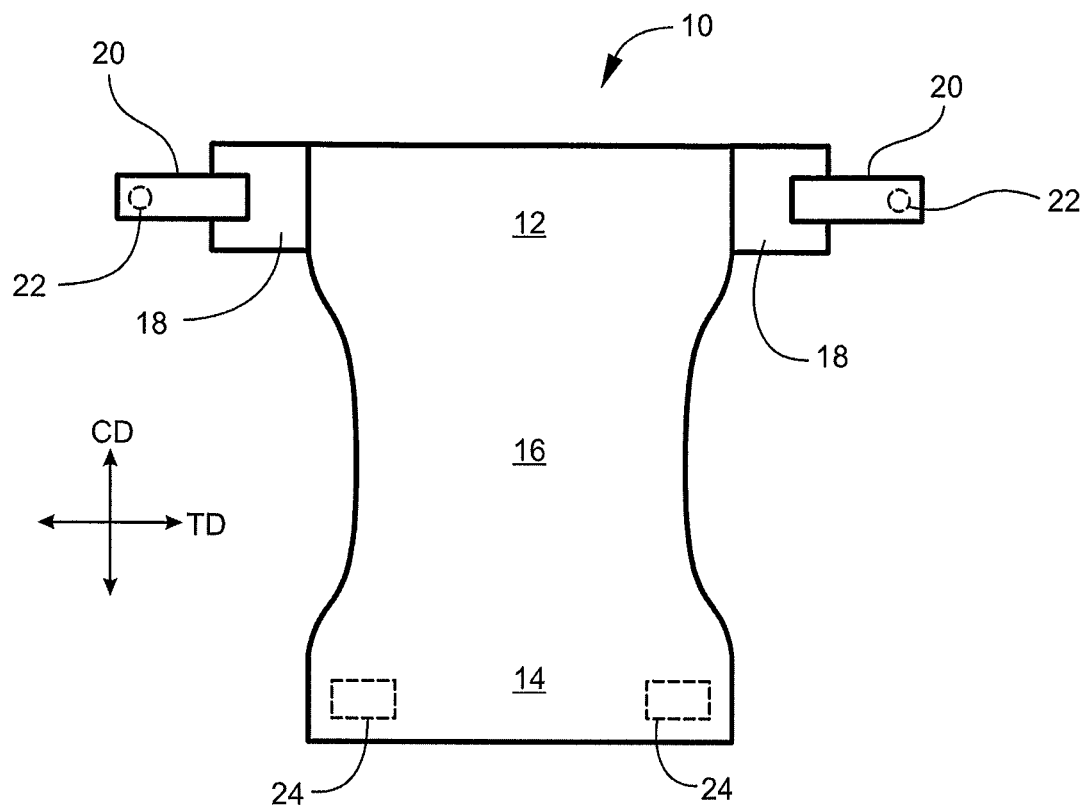
FIG. 1 is a schematic illustration of the instant invention in use in an exemplary hygiene product.

Referring to the drawings, wherein like elements have like numerals, there is shown in FIG. 1 an exemplary hygiene product 10 (the illustrated hygiene product is a diaper). Diaper 10 generally comprises a rear waist portion 12, a front waist portion 14, and an interconnecting portion 16 (having, for example, a 'hour-glass' configuration). At the lateral edges of the rear waist portion 12, there are generally affixed side panels (or ears) 18. At the distal ends of the side panels 18, tabs 20 may be affixed thereto. At the distal ends of tab 20, fastening device 22 may be affixed thereto. On the exterior surface of front waist portion 14, a mating fastening device 24 may be disposed (shown as two elements, but may be a continuous element). Fastening device 22 and mating fastening device 24 co-operate to releasably secure diaper 10 about a wearer, as is well known. Fastening device 22 and mating fastening device 24 may be any known fastening mechanism. Such known fastening mechanisms include, but are not limited to, hook and loop fasteners and adhesive fasteners. In diaper 10, side panels 18 may be elastic (e.g., stretchable in a direction away from rear waist portion 12) and tabs 20 may be non-elastic, or the side panels 18 may be non-elastic and the tabs 20 may be elastic, so that the diaper may be securely fit to the wearer. The stretch laminate disclosed hereinafter may be used in either the side panel ears or the tabs.

Figure 2A:
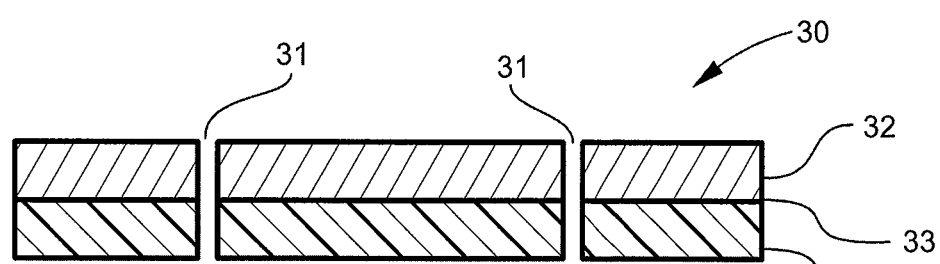
FIGS. 2A and 2B are side elevational views of a cross-section of exemplary stretch laminates with perforations.
Figure 2B:
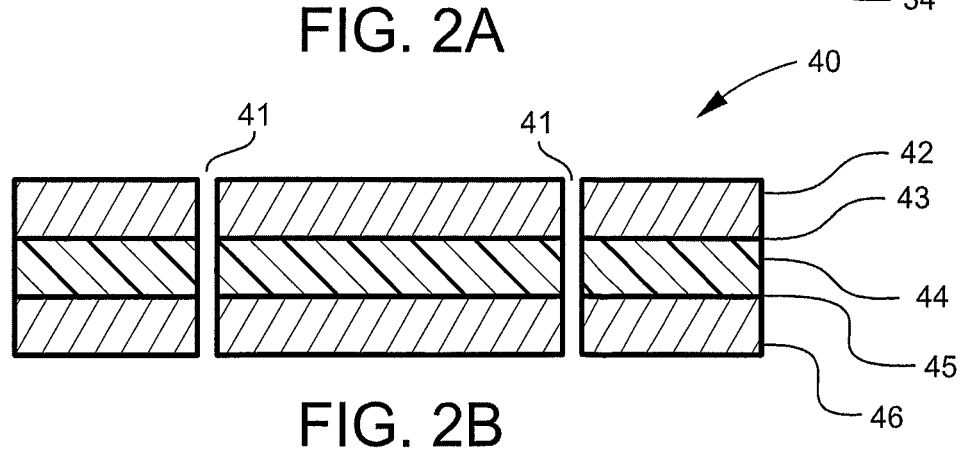

FIGS. 2A and 2B illustrate exemplary embodiments of a stretch laminate with some perforations. In FIG. 2A, a bilayer laminate 30 is shown. Laminate 30 has a nonwoven layer 32 laminated onto an elastic layer 34 with perforations 31. The layers 32, 34 may be adhered to one another via adhesive layer 33 or the adhesive layer may be replaced with another adhering techniques (discussed below). In FIG. 2B, a trilayer laminate 40 is shown. Laminate 40 has two nonwoven layers, 42, 46 sandwiching an elastic layer 44 with perforations 41. The layers 42, 44, and 46 may be adhered to one another via adhesive layers 43, 45 and/or either or both adhesive layers may be replaced with another adhering techniques (discussed below). These stretch laminates are conventional (i.e., may be made of conventional materials) and may be activated or non-activated. Activation may be achieved in any conventional manner, for example, see U.S. Pat. No. 4,834,741—incorporated herein by reference. In this activation process, the laminate, after lamination, is passed between ring (or toothed) rollers to enhance (or activate) the elasticity of the laminate.

Nonwoven, 32, 42, 46 refers to any nonwoven. Such nonwovens include, but are not limited to carded, needled, spunlaced, air-laid, spunbonded, melt blown, combinations of spunbonded and melt blown, and combinations thereof. The fibers of the nonwoven may be staple, filament, or combinations thereof. The fibers of the nonwoven may be polyolefin (PE, PP) or polyester, (PET, PBT), polyamide (nylon) or combinations thereof. The nonwoven may have any basis weight. In one embodiment, the basis weight may be in the range of 5-40 grams per square meter (gsm) and subset therein. In another embodiment, the basis weight may be in the range of 19-30 gsm. In another embodiment the basis weight may be 25±4 gsm. In the trilayer constructions, the basis weights to the two nonwovens may be the same of different. In one embodiment, the first nonwoven may have a basis weight of 22±3 gsm and the other nonwoven may have a basis weight in the range of 27±3 gsm.

Elastic film 34, 44 may be any elastic film. The elastic film may be made of an elastomeric polymer. The elastomeric polymer may be, but is not limited to: styrenic block copolymers, thermoplastic olefins, elastomeric alloys, thermoplastic polyurethanes, thermoplastic co-polyesters, thermoplastic polyamdies, and combinations thereof. Styrenic block copolymers may include, but are not limited to, styrene-isoprene-styrene (SIS) block copolymers, styrene-butene-styrene (SBS) block copolymers, styrene-butadiene rubber (SBR), and combinations thereof. The elastic film may have any basis weight. The basis weight of the film may be in the range of 30-90 gsm and subset therein. In one embodiment, the basis weight of the film may be in the range of 60±10 gsm. The elastic film may be perforated before or after lamination.

The adhesive layer(s) may be made by any adhesive technique. For example, the adhesive technique may use an adhesive and/or another bonding method. Such bonding methods may include: direct lamination (autogenous bonding by contact with molten elastic polymer), thermal bonding (with heat and/or pressure, and continuous or patterned), and/or ultrasonic bonding (continuous or patterned). The adhesive may be elastic or non-elastic. The adhesive may be a continuous sheet between the layers or may be shaped (e.g., shaped refers to: lines—continuous/discontinuous, straight/wavy; dots; patterns). The each adhesive layer may have any basis weight. In one embodiment, the adhesive layer basis weight may be in the range of 5-30 gsm and subset therein. In another embodiment, the adhesive layer basis weight may be in the range of 12±4 gsm. In yet another embodiment, each adhesive layer may have a basis weight of 5-6 gsm.

Figure 3A:
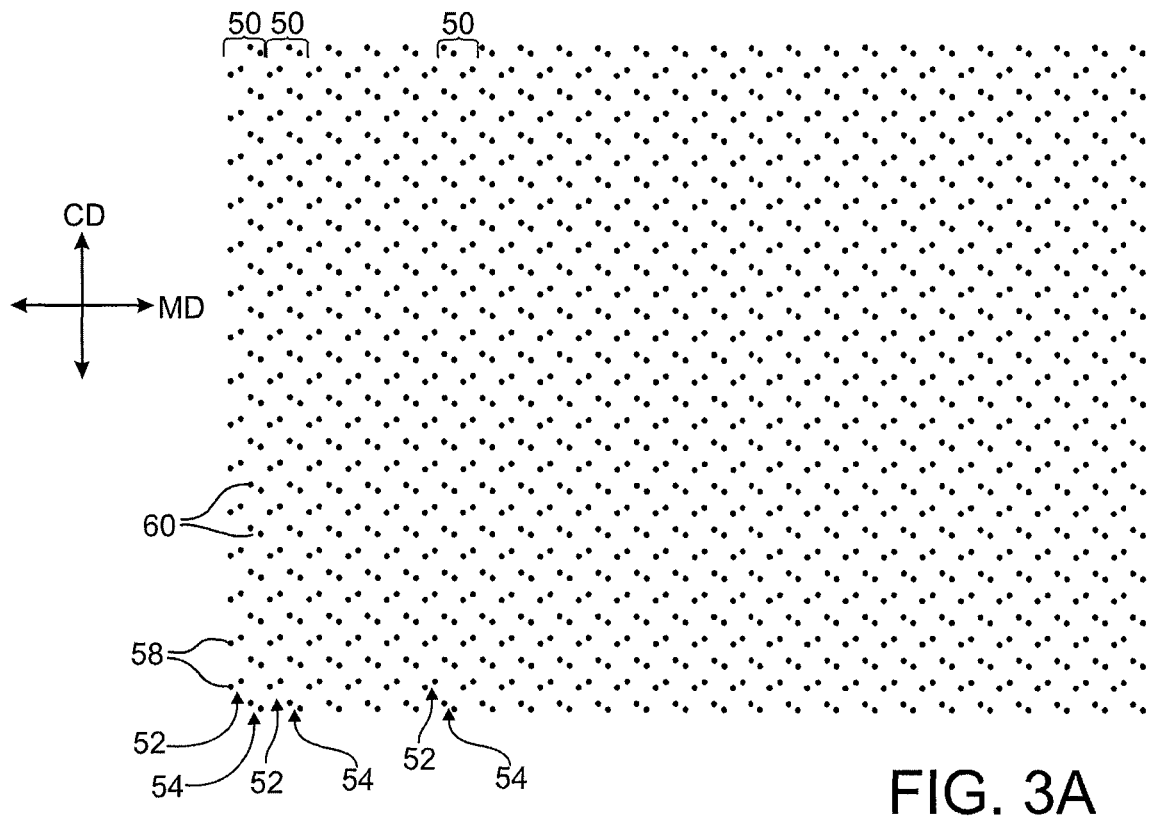
FIG. 3A is a schematic illustration of an embodiment of the invention showing an embodiment of a perforation pattern.
Figure 3B:
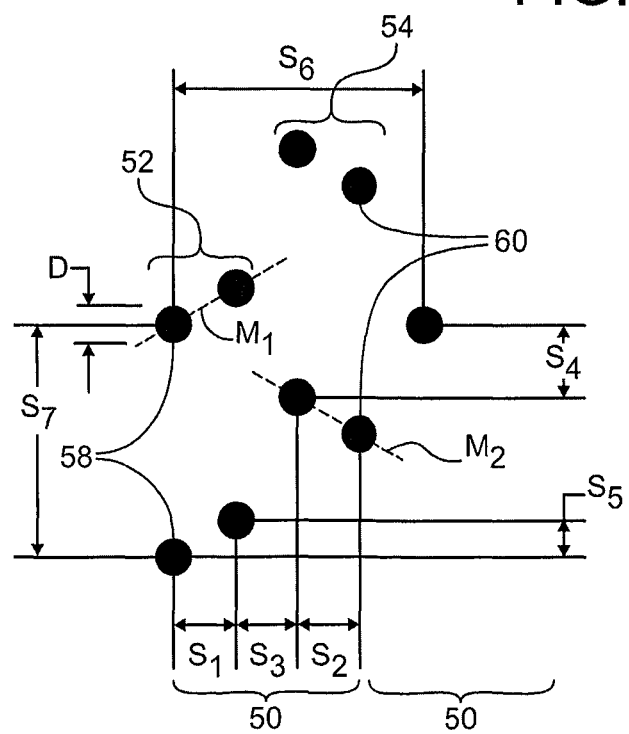
FIG. 3B is an exploded view of a portion of the perforation pattern shown in FIG. 3A.

The perforations (or perforation pattern) will be discussed hereinafter. The perforation pattern is in a stretch laminate (described above). The perforations may be made in the elastic film alone or in the stretch laminate (nonwoven/elastic file or nonwoven/elastic file/nonwoven). FIG. 3A is a schematic illustration of an embodiment of the invention showing the perforation pattern. FIG. 3B is an enlarged view of a portion of the perforation pattern in FIG. 3A (showing two full columns and part of a third column).

Perforations, discussed hereinafter, are referred to a circular, but are not so limited. Perforations may have any shape. Such shapes include, for example; circular, oval (or oblong), rectangular, square, triangular, polygonal, slit (straight or wavy), star, crescent, diamond, or the like.

In FIG. 3A, the perforation pattern includes a pair of columns 50. Each pair of columns 50 includes a first column 52 and a second column 54. Each column 52, 54 has a plurality (or at least two) of pair of perforations stacked one pair on top of the other. For example, column 52 includes perforation pairs 58, and column 54 includes perforation pairs 60.

In FIG. 3B, note: in column 52, the pair of perforations 58 has a slope $M_1$, and in column 54, the pair of perforations 60 has a slope $M_2$. $M_1$ and $M_2$ may be the same or different (i.e., the absolute value of the $M_1$ and $M_2$). $M_1$ may have a positive slope, and $M_2$ may have a negative slope (or vice versa). In another embodiment (not shown), M1 and M2 may be zero, and pairs 58 are located, in their respective columns, between pairs 60, in their respective columns.

The values of spacing, referring to FIG. 3B, given hereinafter is exemplary and is not intended to be limiting, but instead is illustrative of one embodiment of the invention. The space between perforations in a pair is designated by $S_1$ and $S_2$. In one embodiment, $S_1$ and $S_2$ may be the same or different. In one embodiment, $S_1$ and $S_2$ may be 1.7 mm. The space between columns of pairs (or space between adjacent columns) is designated $S_3$. In one embodiment, $S_3$ maybe equal to or different from $S_1$ or $S_2$. In one embodiment, $S_3$ may be 1.7 mm. The space between pairs in a column is designated by $S_4$. In one embodiment, $S_4$ may be 2 mm. The space between a pair of perforations is designated by $S_5$. In one embodiment, $S_5$ may be 1 mm. In one embodiment, $S_4$ is equal to or greater than $S_5$. The space between pairs of columns (leading edge to leading edge) is designated by $S_6$. In one embodiment, $S_6$ may be 6.8 mm. The space between pairs in a column (leading edge to leading edge) is designated $S_7$. In one embodiment, $S_7$ may be greater than or equal to twice (2×) S1. In another embodiment, $S_7$ may be greater than or equal to thrice (3×) S1. In yet another embodiment, $S_7$ may be greater than or equal to 4× S1. A pair of perforations in the first column may be aligned with the space between pairs in the second column (or one pair 58 is between the space separating the pair 60). For example, pair 58 is aligned with the space between pairs 60. The diameter of a perforation is designated by D. In one embodiment, D may be in the range of 0.15-0.90 mm. In another embodiment, D may be 0.55 mm.

Figure 4:
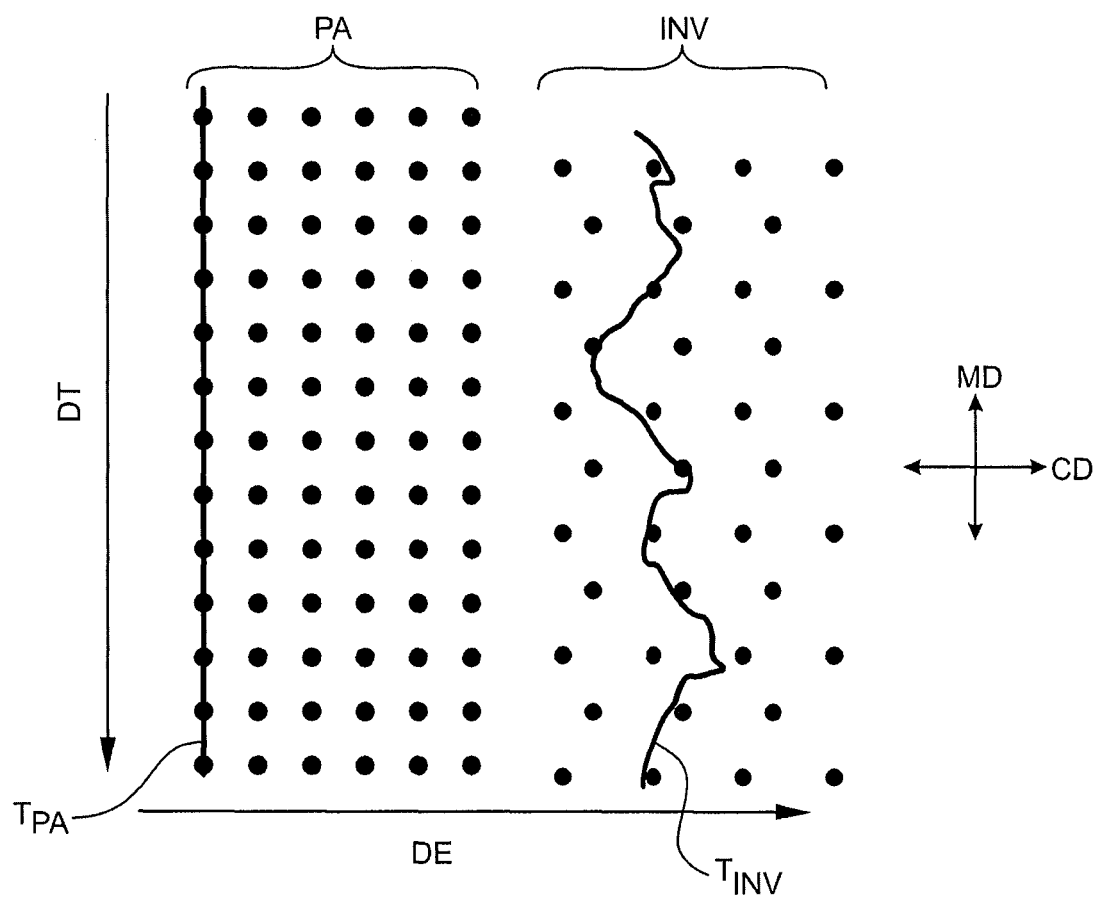
FIG. 4 is a schematic illustration of the operation of the invention (pattern shown in FIG. 3A) in comparison to a prior art perforation pattern.

FIG. 4 is a schematic illustration of the operation of the stretch laminate with the inventive perforation pattern (designated INV) in comparison to a prior art stretch laminate with a linear perforation pattern (designated PA). Direction of elongation is DE and direction of tear is DT. The prior art tear line $T_{PA}$ is straight and follows the first line of perforations perpendicular to the direction of elongation, while the tear line on the inventive pattern $T_{INV}$ is irregular. The irregularity of the line indicates resistance to tearing.

The tear strength of the perforated stretch laminate may be less than the tear strength of the same non-perforated stretch laminate. In one embodiment, the tear strength of the perforated stretch laminate is within about 20% of the same non-perforated stretch laminate. In another embodiment, the tear strength of the perforated stretch laminate is within about 10% of the same non-perforated stretch laminate. In still another embodiment, the tear strength of the perforated stretch laminate is 5-12% less than the same non-perforated stretch laminate. In yet another embodiment (e.g., see FIG. 3A), the tear strength of the perforated stretch laminate is about 7.7% less than the same non-perforated stretch laminate.

Open area refers to the area of the perforations. Open area may be increased or decreased by enlarging or shrinking the diameter of the perforations or may increasing or decreasing the number of perforations. In one embodiment, the open area (i.e., the area of the perforations) of the perforated stretch laminate may be in a range of about 0.5-10.0% (and subsets thereof) of the total surface area of the stretch laminate without tension. In other embodiments, the open area may be in the range of 0.80-5.0%, or 0.80-3.0% or 0.30-2.0%.

In one embodiment, the air permeability of the perforated stretch laminate may be in a range of about 50-1,000 l/m²/sec, and subsets thereof. In other embodiments, the air permeability may be in the range of about 10-500 l/m²/sec or 20-100 l/m²/sec. The permeability of the perforated stretch laminate is, for example, measured according to ISO standard 9237 of 1995 with a pressure of 200 Pa and circular specimens of 20 cm 2.

EXAMPLES

Figure 5:
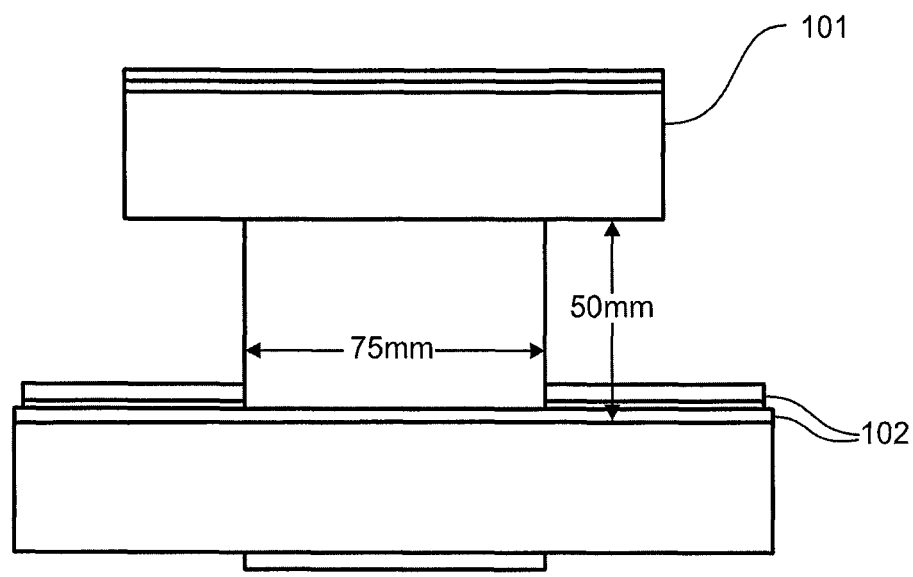
FIG. 5 illustrates the set-up of Method 1.

The following are certain, non-limiting, examples of the inventive perforated stretch laminate, see FIGS. 3A and 3B, by comparison to an equivalent non-perforated stretch laminate. The invention is not limited to the following experimental data.
Test Methods
The following test methods were used in generating the data.
Method 1-Peak Load
Cross direction Peak Load: In FIG. 5, a 75 mm (3 inches) sample (in cross machine direction) is clamped between the jaws 101/102 of a constant rate extension tensile tester (conventional equipment) with the jaws spaced 50 mm (2 inches) apart. The sample is pulled at a rate of 508 mm/minute until the sample breaks. The load at break is the peak load.

Figure 6:
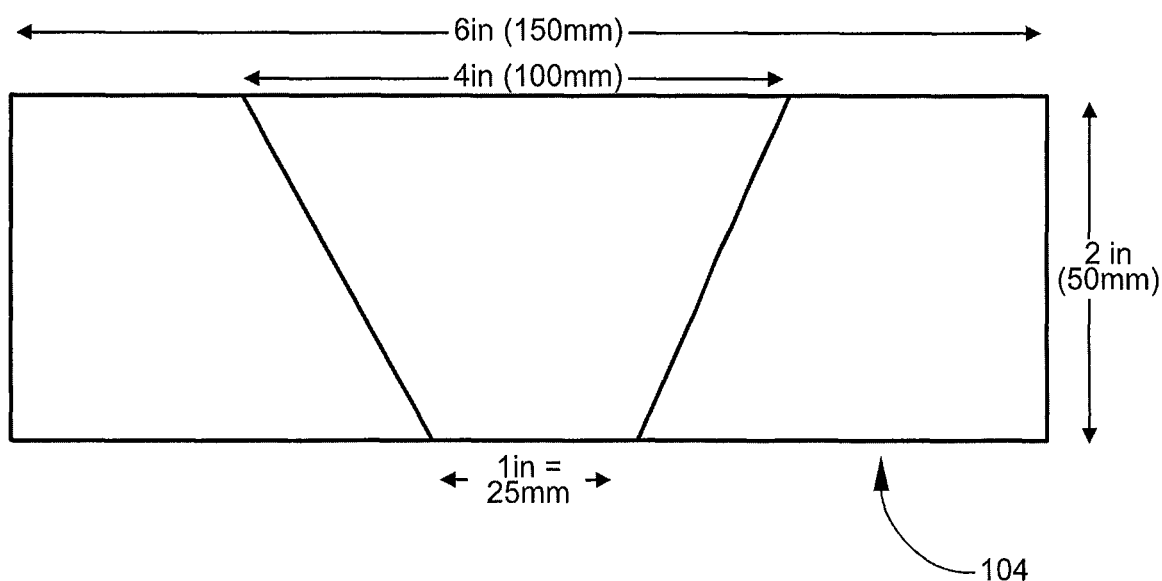
FIGS. 6 and 7 illustrate the sample preparation used in Method 2.
Figure 7:
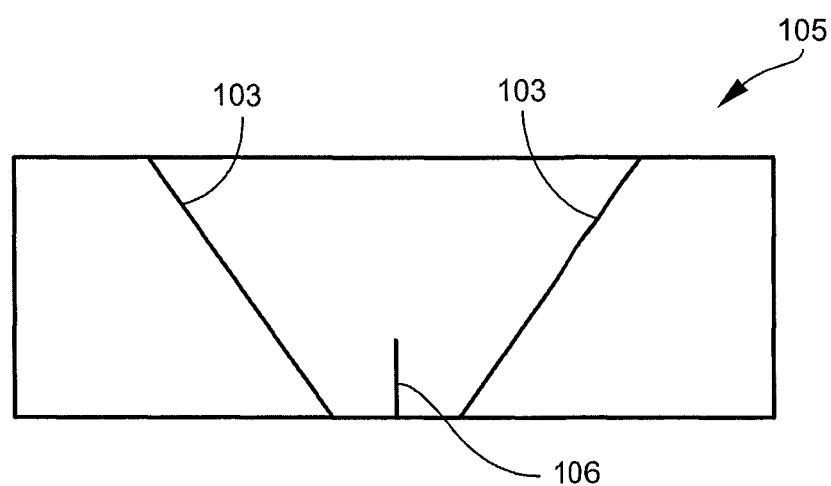
Figure 8:
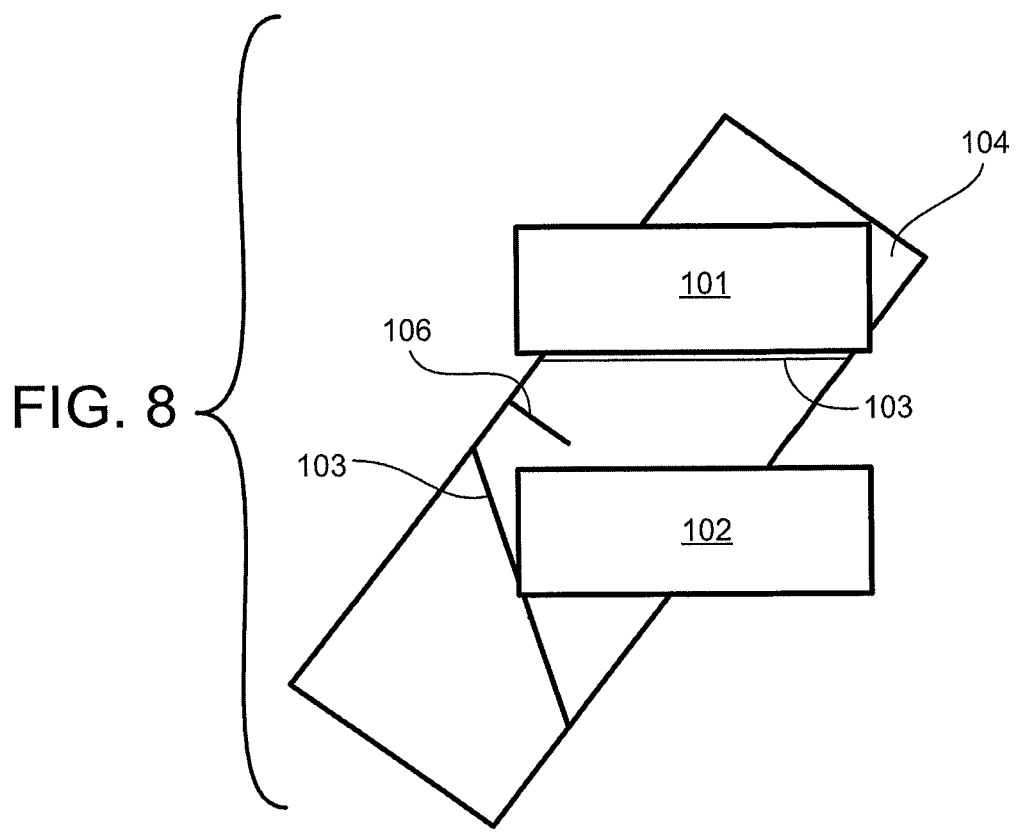
FIGS. 8 and 9 illustrate the set-up of Method 2.
Figure 9:
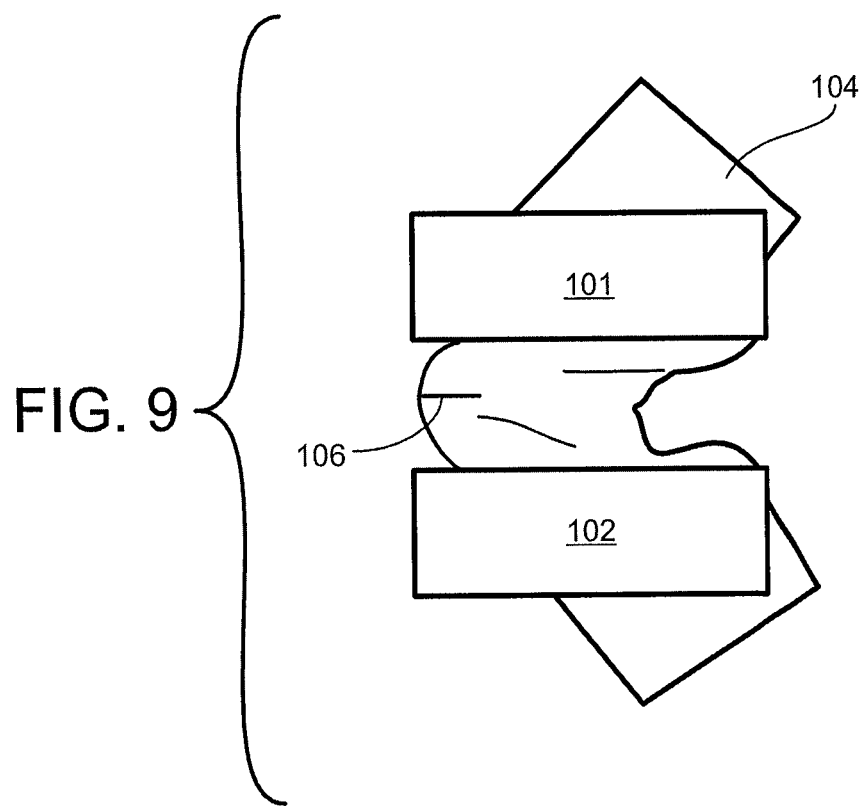

Method 2-Tear Strength
Trapezoid Tear Test (ASTM D5733-99): A 2 inch (50 mm) wide sample 104 is prepared as shown in FIGS. 6 and 7. The 2 inch dimension is in the machine direction of the sample. In FIG. 7, a template 105 is used to draw a pattern (with clamp lines 103) on the sample which is used to orient the sample in the jaws of the constant rate extension tensile tester (conventional equipment). The sample 104 includes a notch (or cut or slit) 106, and the length of the notch is 15 mm. The sample is then clamped between the jaws of a constant rate extension tensile tester as shown in FIGS. 8 and 9 (with lines from the template aligned with the inner edges of the jaws and the notch between the jaws); so that when the sample is pulled, the sample will fail at an angle at one edge of the sample. The sample is pulled at a rate of 508 mm/minute, until the sample breaks. The load at break is the tear strength.
Tensile Property Comparison
In Table 1, certain tensile properties of the inventive stretch laminate are compared to an equivalent non-perforated stretch laminate. A refers to the Tear Strength, B refers to the extension at peak load (i.e., the extension before break); and C refers to the extension at 800 g force. In Table 1, the perforated sample n° 1 (Method A) and the perforated sample n° 2 (Method B) have the same perforation pattern and are obtained by two different processes/Methods of perforation of a non-perforated laminate.

The following observations may be drawn from this data:
1) the tear strength between the inventive sample (INV) and the prior art sample (PA) are similar, in particular the inventive sample is only 15% less of the PA sample, more particular only 10% less, and the average value of the INV is lower;
2) the extension at peak for INV is significantly higher than PA. The INV has a higher stretch than the PA. Thus, a product with higher stretch may be obtained without increasing the amount of activation. This reduces the risks linked to increased activation after lamination, such as risk of tear and uncontrolled hole formations;
3) extension is higher under low force.

At the end of the Table 1, is a line referring to the "gap ratio" of the perforated sample (INV) compare to the non-perforated sample (PA). For example, in column "A-Tear Strength", the gap ratio for the perforated sample n° 1 (Method A) is 92.30%. This value is obtained by dividing 15.99 (the average of "A-Tear Strength" of "Perforated sample n° 1 (Method A) INV") by 17.33 (the average of "A-Tear Strength" of "Non perforated sample PA").
Extension Comparison
In Table 2, three perforated samples are compared. The stretch laminate for each sample is the same prior to extension. The stretch laminate is composed of a tri-layer construction with two nonwovens sandwiching an elastic film (e.g., see FIG. 2B). One nonwoven has a basis weight of 22 gsm and the other has a basis weight of 27 gsm. Both nonwovens are carded nonwovens. The elastic film has a basis weight of 60 gsm. The adhesive (between each layer) has basis weight of 12 gsm. The perforation patterns are the same, see FIGS. 3A and 3B, prior to extension. The Samples 1, 2 and 3 in Table 2 correspond, respectively, to a laminate at relaxed state, at extension of 147% and at extension of 160%.

The following observations may be drawn from the 1, 2, 3 of Table 2:
1) the hole dimension in the direction perpendicular to the tear direction is substantially in the range of 0-200% extension (or in the range of 0-160% extension or in the range of 10-160% extension);

2) as the samples are pulled in the cross machine direction, the holes elongate from a circular shape to an oval shape and the hole spacing increases (both in the cross machine direction). Since the hole area increases, the air permeability likewise increases, but there are fewer holes per unit area;
3) the hole dimension in the machine direction appears to remain constant during the extensions noted;
4) after relaxation, the sample had a dimension of 75 mm (MD)×100 mm (CD), elongation was in the CD. The initial elastic film was less than 50 mm, but after activation, the width was 80 mm. The objective is to meet breathability targets (obtained via perforations (holes)), but maintain tear strength. Therefore, it preferred that the minimum number of perforations per unit area is used. One way to achieve the foregoing is to increase hole spacing in the MD and decrease hole spacing in the CD (direction of elongation).

From the data in Table 2, the following conclusions may be drawn:
1) during extension, the holes become wider in the CD, the hole area increases, and the air permeability increases;
2) hole spacing in the CD increases, this should increase tear strength;
3) hole spacing in the MD decreases only slightly with elongation in the CD, so hole spacing in the MD may be maintained for elongation in the CD.

The present invention may be embodied in other forms without departing from the spirit and the essential attributes thereof, and, accordingly, reference should be made to the appended claims, rather than to the foregoing specification, as indicated the scope of the invention.

We claim:
1. A method for reducing or preventing tearing in a stretch laminate when the stretch laminate is stretched in a stretching direction, comprises the steps of:
   providing the stretch laminate with a pattern of perforations, each perforation having a shape selected from the group of circular, oval, rectangular, square, triangular, polygonal, star, crescent, and diamond,
   the pattern of perforations has at least two aligned columns,
   a first column having a plurality of pairs of perforations stacked one pair above the other pair, the perforations in each pair sloping in a first direction at an angle to the stacking direction and having a leading edge defined by the lowest point of the shape of one perforation in the stacking direction and a trailing edge formed by the highest point of the shape of the other perforation in the stacking direction, and a first space separating the leading edge of one pair in the first column from the trailing edge of an adjacent pair in the first column,
   a second column having a plurality of pairs of perforations stacked one pair above the other pair, the perforations in each pair sloping in a second direc-

TABLE 1

|  | A - Tear Strength | | | B - Extension at Peak | | | C - Extension at 800 g | | |
| --- | --- | --- | --- | --- | --- | --- | --- | --- | --- |
|  | Perforated sample no 1 (Method A) INV (N) | Non perforated sample PA (N) | Perforated sample no 2 (Method B) INV (N) | Perforated sample no 1 (Method A) INV (mm) | Non perforated sample PA (mm) | Perforated sample n°2 (Method B) INV (mm) | Perforated sample no 1 (Method A) INV (mm) | Non perforated sample PA (mm) | Perforated sample no 2 (Method B) INV (mm) |
| 1 | 9.79 | 14.41 | 12.39 | 133.44 | 89.4 | 115.16 | 118.96 | 48.19 | 81.42 |
| 2 | 14.53 | 21.15 | 12.97 | 124.46 | 113.13 | 117.91 | 71.42 | 46.85 | 75.18 |
| 3 | 16.33 | 13.92 | 26.49 | 147.82 | 74.15 | 224.33 | 77.38 | 46.95 | 78.17 |
| 4 | 17.42 | 19.15 | 16.42 | 156.37 | 130.88 | 137.67 | 77.11 | 51.76 | 76.64 |
| 5 | 21.21 | 16.98 | 26.39 | 195.99 | 95.75 | 225.48 | 78.03 | 51.62 | 74.80 |
| 6 | 17.66 | 17.18 | 16.33 | 170.69 | 99.33 | 128.01 | 81.89 | 49.04 | 68.90 |
| 7 | 14.77 | 19.52 | 20.34 | 120.40 | 103.12 | 158.59 | 69.33 | 44.41 | 71.14 |
| 8 | 14.68 | 18.20 | 8.49 | 127.44 | 93.16 | 102.29 | 71.19 | 43.80 | 71.16 |
| 9 | 18.56 | 15.74 | 15.18 | 175.78 | 76.71 | 130.32 | 74.66 | 45.08 | 79.27 |
| 10 | 16.07 | 17.03 | 13.71 | 139.87 | 102.12 | 104.37 | 70.55 | 48.62 | 67.14 |
| 11 | 19.19 |  |  | 155.20 |  |  | 63.00 |  |  |
| 12 | 11.71 |  |  | 123.60 |  |  | 66.51 |  |  |
| Ave. | 15.99 | 17.33 | 16.87 | 147.59 | 97.78 | 144.41 | 76.67 | 47.63 | 74.38 |
| St Dev | 3.18 | 2.27 | 5.91 | 23.97 | 16.60 | 45.47 | 14.34 | 2.77 | 4.68 |
| Max | 21.21 | 21.15 | 26.49 | 195.99 | 130.88 | 225.48 | 118.96 | 51.76 | 81.42 |
| Min | 9.79 | 13.92 | 8.49 | 120.40 | 74.15 | 102.29 | 63.00 | 43.80 | 67.14 |
| Note | 92.30% |  | 97.36% | 150.95% |  | 147.70% | 160.96% |  | 156.16% |
|  | Tear | | | | | | Reduction of extension | | |

Note:
Gap ratio of Invention (INV) compared to prior art (PA): [INV/PA].

TABLE 2

| Sample | Amount Elongated | Elongation rate | # of Holes per cm² | Dimensions of Hole mm | Area of Hole mm² | Area of holes mm² | % Open | Air Permeability, l/m²/sec | Distance between two points in MD mm | % compare to sample 1 | Distance between two points in CD mm | % compare to sample 1 |
| --- | --- | --- | --- | --- | --- | --- | --- | --- | --- | --- | --- | --- |
| 1 | 0 | 0% | 10 | 0.5 × 0.5 | 0.196 | 1.96 | 1.96% | 216 | 6 |  | 7.3 |  |
| 2 | 35 mm | 147% | 8 | 0.5 × 1.3 | 0.5105 | 4.084 | 4.08% | 473 | 5.7 | 95% | 10.6 | 145% |
| 3 | 45 mm | 160% | 7 | 0.5 × 1.5 | 0.5894 | 4.1258 | 4.13% | 465 | 5.7 | 95% | 12 | 164% | tion at an angle to the stacking direction and having a leading edge defined by a lowest point of the shape of one perforation in the stacking direction and a trailing edge formed by a highest point of the shape of the other perforation in the stacking direction, and a second space separating the leading edge of one pair in the second column from the trailing edge of an adjacent pair in the second column, the one pair of perforations in the first column from its leading edge to its trailing edge is located within the second space between the one pair of perforations and the adjacent pair of perforations in the second column, and a third space between the first column and the second columns being less than the first space or second space.

2. The method of claim 1, wherein a distance formed between the leading edge and the trailing edge in the stacking direction of the one pair of perforations in each the first column and the second column defines a height and each of the first space and second space is equal to the height.

3. The method of claim 1, wherein a distance formed between the leading edge and the trailing edge in the stacking direction of the one pair of perforations in each the first column and the second column defines a height and each the first space and second space is greater than the height.

4. The method of claim 1, wherein the stretch laminate has an open area in the range of about 0.5 to 10.0%.

5. The method of claim 1, wherein the stretch laminate has an air permeability in a range of about 50-1,000 l/m²/sec.

6. The method of claim 1, wherein wherein the stretch laminate has a peak load of no less than 80% of the peak load of a non-perforated stretch laminate.

7. The method of claim 1, wherein the stretch laminate has an extension at peak load greater than an extension at peak load of a non-perforated stretch laminate.

8. The method of claim 1, wherein the stretch laminate comprises:

a first nonwoven and an elastic layer affixed to the first nonwoven.

9. The method of claim 8, wherein the stretch laminate further comprises a second nonwoven, and the elastic layer is sandwiched between the first nonwoven and the second nonwoven.

10. The method of claim 1, wherein each of the first space and second space is greater than or equal to twice a space between the perforations in the one pair of perforations in each the first column and the second column.

11. The method of claim 1, wherein the first direction and the second direction are different.

12. The stretch laminate formed by the method of claim 1 for use in a hygiene product, comprises:

a laminate with a nonwoven layer and an elastic layer, the laminate having a the perforation pattern, wherein the perforation pattern is adapted to resists tearing in a direction perpendicular to a directions of stretching.

13. The stretch laminate of claim 12, wherein a distance formed between the leading edge and the trailing edge in the stacking direction of the one pair of perforations in each the first column and the second column defines a height and each the first space and second space is equal to the height.

14. The stretch laminate of claim 12, wherein a distance formed between the leading edge and the trailing edge in the stacking direction of the one pair of perforations in each the first column and the second column defines a height and each the first space and second space is greater than the height.

15. The stretch laminate of claim 12, wherein the stretch laminate has an open area in the range of about 0.5 to 10.0%.

16. The stretch laminate of claim 12, wherein the stretch laminate has an air permeability in-the a range of about 50-1,000 l/m²/sec.

17. The stretch laminate of claim 12, wherein the stretch laminate has a peak load of no less than 80% of the peak load of a non-perforated stretch laminate.

18. The stretch laminate of claim 12, wherein the stretch laminate has an extension at peak load greater than an extension at peak load of a non-perforated stretch laminate.

19. The stretch laminate of claim 12, wherein the stretch laminate comprises: the nonwoven layer being a first nonwoven and an the elastic layer affixed to the first nonwoven.

20. The stretch laminate of claim 12, wherein the stretch laminate further comprises a second nonwoven, and the elastic layer is sandwiched between the first nonwoven and the second nonwoven.

21. The stretch laminate of claim 12, wherein a space (S7) between pairs of perforations in the column each of the first space and second space is greater than or equal to twice a space (S1) between the perforations in the one pair of perforations in each the first column and the second column.

22. The stretch laminate of claim 12, wherein the first direction and the second direction are different.

* * * * *